US010471142B2

United States Patent
Basta et al.

(10) Patent No.: US 10,471,142 B2
(45) Date of Patent: Nov. 12, 2019

(54) COMBINATION THERAPY USING IMMUNOGLOBULIN AND C1-INHIBITOR

(71) Applicants: Milan Basta, Potomac, MD (US); Xinzhi Chen, Wexford, PA (US); Mark Mattson, Bel Air, MD (US)

(72) Inventors: Milan Basta, Potomac, MD (US); Xinzhi Chen, Wexford, PA (US); Mark Mattson, Bel Air, MD (US)

(73) Assignees: CSL BEHRING GMBH, Marburg (DE); THE GOVERNMENT OF THE UNITED STATES OF AMERICA, Rockville, MD (US)

( * ) Notice: Subject to any disclaimer, the term of this patent is extended or adjusted under 35 U.S.C. 154(b) by 407 days.

(21) Appl. No.: 14/346,478

(22) PCT Filed: Sep. 21, 2012

(86) PCT No.: PCT/EP2012/068643
§ 371 (c)(1),
(2) Date: Mar. 21, 2014

(87) PCT Pub. No.: WO2013/041677
PCT Pub. Date: Mar. 28, 2013

(65) Prior Publication Data
US 2014/0234293 A1     Aug. 21, 2014

Related U.S. Application Data

(60) Provisional application No. 61/538,832, filed on Sep. 24, 2011.

(51) Int. Cl.
| A61K 39/395 | (2006.01) |
| A61K 45/06 | (2006.01) |
| A61K 38/55 | (2006.01) |
| C07K 16/06 | (2006.01) |
| A61K 38/57 | (2006.01) |
| A61K 39/00 | (2006.01) |

(52) U.S. Cl.
CPC ........ *A61K 39/39516* (2013.01); *A61K 38/55* (2013.01); *A61K 38/57* (2013.01); *A61K 45/06* (2013.01); *C07K 16/06* (2013.01); *A61K 2039/505* (2013.01)

(58) Field of Classification Search
None
See application file for complete search history.

(56) References Cited

U.S. PATENT DOCUMENTS

| 4,915,945 | A | 4/1990 | Pelzer et al. |
| 5,827,832 | A | 10/1998 | Sandage, Jr. et al. |
| 5,939,389 | A | 8/1999 | Eisele et al. |
| 6,248,365 | B1 | 6/2001 | Romisch et al. |
| 7,053,176 | B1 | 5/2006 | Hafner et al. |
| 8,632,773 | B2 * | 1/2014 | Kaermann ............... C07K 1/22 424/130.1 |
| 2007/0081992 | A1 * | 4/2007 | Pardridge ............ C07K 14/475 424/143.1 |
| 2010/0143325 | A1 | 6/2010 | Gurewich |
| 2010/0330071 | A1 | 12/2010 | Teschner et al. |

FOREIGN PATENT DOCUMENTS

| WO | WO 2004/075837 A2 | 9/2004 |
| WO | WO 2007/073186 A2 | 6/2007 |
| WO | WO 2007/073186 A3 | 6/2007 |

OTHER PUBLICATIONS

Scheinfeld et al., Intravenous Immunoglobulin, Medscape Reference Drugs, Disease & Procedures emedicien.medscape.com/article/210367-overview; Intravenous Immunoglobulin: Overview, Used of Intravenous Immunoglobulin, Pharmacology and Monitoring pp. 1-13, downloaded Jun. 8, 2016.*
Strom et al. in Therapeutic Immunology, edited by Austen et al., Blackwell Science, Cambridge MA, 1996; see pp. 451-456.*
Adeoye et af., "Recombinant Tissue-Type Plasminogen Activator Use for Ischemic Stroke in the United States", Stroke 42(7):1952-1955 (2011).
Arumugam et al., "Intravenous immunoglobulin (IVIG) protects the brain against experimental stroke by preventing complement-mediated neuronal cell death", PNAS 104(35): 14104-14109 (2007).
De Simoni et al., "Neuroprotection by Complement (C1) Inhibitor in Mouse Transient Brain Ischemia", J. Cereb. Blood Flaw Metab. 23(2): 232-239 (2003).
Longhi et al., "C1-inhibitor attenuates neurobehavioral deficits and reduces contusion volume after controlled cortical impact brain injury in mice", Crit. Care Med. 37(2): 659-665 (2009).
De Simoni et al., "The Powerful Neuroprotective Action of C1-Inhibitor on Brain Ischemia-Reperfusion Injury Does Not Require C1q", Am J Pathol 164: 1857-1863 (2004).
Akita et al., English-language abstract of "The effect of C1 esterase inhibitor on isohernia: reperfusion injury in the rat brain" No To Shinkei 53: 641-644 (2001).
Gesuete et al., "Recombinant C1 Inhibitor in Brain Ischemic Injury", Ann Neurol 66:332-342 (2009).
Köhler and Milstein, "Continuous cultures of fused cells secreting antibody of predefined specificity", Nature 256: 495-497 (1975).
Kozbor et al., "The production of monoclonal antibodies from human lymphocytes", Immunology Today 4: 72-79 (1983).
Cole et al. Monoclonal Antibodies and Cancer Therapy, Alan R. Liss, Inc. (1985), pp. 33-74.
Bundesarztekammer, Dtsch Arztebl 97: B-864 (2000).
Shah et al., "Capillary Leak Syndrome after Open Heart Surgery for Congenital Heart Defects: Therapy with C1-Inhibitor", Biomed Prog. 9:13-16 (1996).
Horstick et al., "Application of C1-Esterase Inhibitor During Reperfusion of Ischemic Myocardium", Circulation 104: 3125-3131 (2001).
Wang et al., "Gene inactivation of $Na^{30}/H^+$ exchanger isoform 1 attenuates apoptosis and mitochondrial damage following transient focal cerebral ischemia", Eur. J. Neurosci. 28(1): 51-61 (2008).

(Continued)

*Primary Examiner* — Phillip Gambel
(74) *Attorney, Agent, or Firm* — Finnegan, Henderson, Farabow, Garrett & Dunner, L.L.P.

(57) ABSTRACT

Methods are disclosed for treating cerebral ischemia using a combination of C1-INH and immunoglobulin, such as human plasma derived immunoglobulin (IVIG).

17 Claims, 4 Drawing Sheets

(56) References Cited

OTHER PUBLICATIONS

Murakami et al., "Mitochondrial Susceptibility to Oxidative Stress Exacerbates Cerebral Infarction That Follows Permanent Focal Cerebral Ischemia in Mutant Mice with Manganese Superoxide Dismutase Deficiency", J. Neurosci. 18: 205-213 (1998).
X. Chen et al.. "Inhibition and Scavenging of Complement as Therapeutic Targets in the Mouse Model of Actuelschernic Stroke", Annals of Neurology: vol. 70, No. Suppl. 15, pp. 54-55, XP9164996 (2011).
T. Arumugam et al., "Neuroprotection in Stroke by Complement Inhibition and Immunoglobu in Therapy", Neuroscience, vol. 158, No. 3, pp. 1074-1089 (2009).
T. Arumugam et al., "Intravenous immunoglobulin (IVIG) protects the brain against experimental stroke by preventing complement-mediated neuronal cell death", Proceedings of the National Academy of Sciences, vol. 104, No. 35, pp. 14104-14109 (2007).
T. Arumugam et al.; "Targeting ischemic brain injury with intravenous immunoglobulin", Expert Opinion on Therapeutic Targets, vol. 12, No. 1, pp. 19-29 (2008).
A, Heimann et al, "C1-esterase inhibitor reduces infarct vol. after cortical vein occlusion", Brain Research, vol. 838, No. 1-2, pp. 210-213 (1999).
N. Akita et al.. "Protective Effective of C1 Esterase Inhibitor on Reperfusion Injury in the Rat Middle Cerebral Artery Occlusion Model", Neurosurgery, vol. 52, No. 2, pp. 395-401 (2003).
R. Gesuete et al "Recombinant C1 Inhibitor in Brain Ischemic Injury", Annals of Neurology, vol. 66, No. 3, pp. 332-342 (2009).
C. Storini et al., "C1-inhibitor protects against brain ischemia-reperfusion injury via inhibition of cell recruitment and inflammation"; Neurobiology of Disease, vol. 19, No. 1-2, pp. 10-17 (2005).
T. Woodruff et ai., "Pathophysiology, treatment, and animal and cellular models of human ischemic stroke", Molecular Neurodegeneration, vol. 6, No. 1, 19 pages (2011).
International Search Report from the European Patent Office for International Application No. PCT/EP2012/068643 dated Jun. 12, 2012.
Witten Opinion of the International Search Authority from the European Patent Office for International Application No. PCT/EP2012/068643 dated Jun. 12, 2012.
Chen, et al., "Therapeutic efficacy of natural inhibitors of the complement cascade in a mouse model of focal ischemic stroke," Society for Neuroscience—presentation abstract, vol. 41 (2011).
Adams, Jr., Harold P., "Stroke: a vascular pathology with inadequate management," J. Hypertens, (Suppl 21): S3-S7 (2003).
Akita N. et al., "The effect of C 1 esterase inhibitor on ischemia: reperfusion injury in the rat brain," No To Shinkei, 53:641-644 (2001).
Australian Examination Report for Australian Patent Application No. 2012311483 dated Jul. 29, 2014 (4 pages).

Brea et al., "Toll-like receptors 2 and 4 in ischemic stroke: outcome and therapeutic values," Journal of Cerebral Blood Flow & Metabolism, 31:1424-1431 (2011).
Chamorro et al., "The immunology of acute stroke," Neurology, 8:401-410 (Jul. 2012).
Cojocaru et al., "Changes in Plasma Levels of Complement in Patients with Acute Ischemic Stroke," Rom, J. Intern. Med., 46(1):77-80 (2008).
Culmsee et al., "Combination Therapy in Ischemic Stroke: Synergistic Neuroprotective Effects of Memantine and Clenbuterol," Stroke, 35:1197-1202 (2004).
Davis III et al., "Biological activities of C1 inhibitor," Molecular Immunology, 45-4057-4063 (2008).
D'Ambrosio et al., "The Role of the Complement Cascade in Ischemia/Reperfusion Injury: Implications for Neuroprotection,"Molecular Medicine, 7(6):367-382 (2001).
Gancz et al., "Involvement of the c-jun N-terminal kinases JNK1 and JNL2 in complement-mediated cell death," Molecular Immunology, 47:310-317 (2009).
De Keyser et al., "Clinical trials with neuroprotective drugs in acute ischaemic stroke: are we doing the right thing?" TINS, 22(12): 535-540 (1999).
De Keyser et al., "Neuroprotection in acute ischemic stroke," Acta. Neurol. Belg., 105:144-148 (2005).
Hajishengallis et al., "Crosstalk pathways between Toll-like receptors and the complement system," Trends Immunol., 31:154-163 (2010).
Jung et al., "Augmentation of nitrite therapy in cerebral ischemia by NMDA receptor inhibition," Biochemical and Biophysical Research Communications, 378. 507-512 (2009).
Lloyd-Jones et al., "Heart Disease and Stroke Statistics—2009 Update: A Report from the American Heart Association Statistics Committee and Stroke Statistics Subcommittee," Circulation, 119:e21-181 (2009).
Longa et al., "Reversible middle cerebral artery occlusion without craniectomy in rats," Stroke, 20:84-91 (1989).
Ma et al., Synergistic protective effect of caspese inhibitors and bFGF against brain injury induced by transient focal ischaemia, British Journal of Pharmacology, 133:345-350 (2001).
Okun et al., "Toll-like receptor signaling in neural plasticity and disease," Trends Neurosci., 34(5):289-81 (2011).
Okuno et al., "The c-Jun N-Terminal Protein Kinase Signaling Pathway Meidates Bax Activation and Subsequent Neuronal Apoptosis through Interaction with Bim after Transient Focal Cerebral Ischernia." The Journal of Neuroscience, 24(38):7879-7887 (2004).
Osthoff et al., "Mannose-Binding Lectin Deficiency Is Associated With Smaller Infarction Size and Favorable Outcome in ischemic Stroke Patients," PloS One, 6(0);e21338 (2011).
Szeplaki et al., "Strong complement activation after acute ischemic stroke is associated with unfavorable outcomes," Atherosclerosis, 204:315-320 (2009).
Tang et al., "Pivotal role for neuronal Toil-like receptors in ischemic brain injury and functional deficits," PNAS, 104(34):13798-13803 (2007).

\* cited by examiner

COMBINATION THERAPY USING IMMUNOGLOBULIN AND C1-INHIBITOR

This application claims priority under 35 U.S.C. § 119 to U.S. Provisional Patent Application No. 61/538,832, filed on Sep. 24, 2011, which is hereby incorporated by reference in its entirety.

This invention was made in part with government support under Collaborative Agreement #29466-09, awarded by The National Institute on Aging, National Institutes of Health. The government has certain rights in the invention.

The present disclosure relates generally to the use of C1-Inhibitor (C1 esterase inhibitor or C1-INH) and immunoglobulin, such as plasma-derived immunoglobulin G (IVIG), in the treatment of cerebral ischemia.

Acute ischemic stroke (AIS) is a significant public health problem, causing a high rate of death and permanent neurological deficits in survivors. Current interventional treatment, in the form of enzymatic thrombolysis, benefits only a small percentage of patients. Less than 6% of all AIS patients in the US are eligible for current standard of care treatments, such as enzymatic thrombolysis by recombinant tissue plasminogen activator rtPA, primarily due to the short therapeutic window (e.g., usually about 1 hour following stroke). Adeoye O, Hornung R, Khatri P, Kleindorfer D. *Stroke* 42(7):1952-1955 (2011). Treatments such as rtPA can also increase the risk of inducing brain hemorrhage in a patient. Thus, there is a need for improved treatments for AIS, and particularly for treatments that are effective when administered at later times after the stroke.

The complement system is a proteolytic cascade of about 30 circulating plasma proteins and associated cell membrane proteins. The plasma proteins are generally synthesized in the liver and normally circulate as inactive precursors. Precursor cleavage by complement proteases initiates the cytokine signaling cascades responsible for various innate immune responses, including inflammation. Complement activation is implicated in a variety of immune-inflammatory responses, including inflammation associated with cerebral ischemia.

During reperfusion following cerebral ischemia, the restoration of circulation can lead to inflammatory and oxidative damage to brain tissue. White blood cells entering the tissue upon reperfusion release a host of inflammatory factors including interleukins and free radicals. The reintroduction of oxygen with the returning blood can also damage cells and plasma membranes. The complement system has been implicated in the initiation of the ischemic cascade in the brain that results in reperfusion injury. Thus, techniques for inhibiting or modulating the complement system could offer opportunities to treat or prevent reperfusion injury.

Plasma-derived immunoglobulins such as intravenous immunoglobulin G (IVIG) are intravenously-administered blood products containing pooled immunoglobulins extracted from multiple blood donors. IVIG is indicated for use in various immune deficiency and inflammatory diseases. IVIG has been shown to scavenge active complement fragments in the brain and protects against the damage associated with cerebral ischemia and reperfusion. Arumugam et al., *PNAS* 104(35): 14104-14109 (2007).

C1-Inhibitor (C1-INH) is a serine protease inhibitor that prevents spontaneous activation of circulating proteases associated with the complement system, in particular C1r and C1s, as well as MASP-1 and MASP-2. Given the central role of C1-INH in regulating the complement classic pathway and the involvement of complement-mediated inflammation in reperfusion injury, C1-INH administration has been investigated for its effects on neurological deficit and infarction size following stroke. De Simoni et al., *J. Cereb. Blood Flow Metab.* 23(2): 232-239 (2003); see also Longhi et al., *Crit. Care Med.* 37(2): 659-665 (2009). Previous research has shown that C1-INH has potent neuroprotective properties in mouse models of cerebral ischemia. Suggested mechanisms associated with C1-INH neuroprotection include 1) complement inhibition, 2) attenuation of the inflammatory response to an injury, 3) attenuation of apoptosis, and 4) decrease of leukocyte-endothelial cell adhesion. Inhibition of complement activation by plasma derived C1-INH was shown to be beneficial in mouse as well as rat. De Simoni et al., *Am J Pathol* 164: 1857-1863 (2004); Akita et al., *No To Shinkei* 53: 641-644 (2001). However, the therapeutic window observed in these studies was less than one hour post ischemia. Id. This is in contrast to a recent finding that recombinant C1-INH is capable of reducing the brain infarction size at later time points (e.g., when given up to 18 hours following MCAO). Gesuete et al., *Ann Neurol* 66:332-342 (2009). The general notion until now was that plasma-derived C1-INH, due to its short therapeutic window, is not as promising as recombinant C1-INH for treating stroke in humans.

While animal experiments have suggested that C1-INH and IVIG individually may be effective in modulating the effects of reperfusion injury in the brain, there remains a need to develop more effective, lower dose, and cost-efficient methods for treating reperfusion injury associated with cerebral ischemia. Accordingly, disclosed here is a combination therapy employing C1-INH and immunoglobulins such as IVIG to treat, reduce, or prevent reperfusion injury and inflammatory damage associated with cerebral ischemia, either by prophylactic administration or administration at timepoints following ischemia. In some embodiments, the use of a combination of C1-INH and immunoglobulins such as IVIG can be used to treat or prevent reperfusion injury and inflammation damage at later timepoints, where either component alone provides less therapeutic effects. In some embodiments, the combination was administered up to about 6 hours after cerebral ischemia or at less than maximal doses of either component while providing for beneficial effects. In some embodiments the combination may be administered later than 6 hours after cerebral ischemia. Employing the combination of C1-INH and immunoglobulins such as IVIG could thus lead to enhanced therapeutic outcomes while allowing for reduced treatment dosages, thereby lowering cost as well as reducing the risk of adverse reaction to treatment compounds.

BRIEF DESCRIPTION OF THE DRAWINGS

FIG. 1. C1-INH dose response curve. Groups of mice (n=12-21) were treated at 1 hour after the end of the ischemic period (I) with decreasing doses of C1-INH at 300 U/Kg (7.6 U per animal), 150 U/Kg (3.8 U per animal) and 75 U/Kg (1.9 U per animal). C1-INH concentration (U/Kg) is plotted on the horizontal axis against reduction of infarction volume (%) on the vertical axis.

FIG. 2. IVIG dose response curve. Groups of animals (12-22) were treated 1 hour after ischemia with decreasing doses of IVIG, starting with 1 g/kg of body weight and continuing with decreasing half doses—0.5 g/Kg and 0.25 g/Kg (or mg/g considering the average body weight of an adult mouse to be 25-30 g). IVIG doses (g/Kg) are plotted on the horizontal axis against reduction of infarction volume (%) on the vertical axis.

FIG. 3. Combination C1-INH/IVIG treatment. A single IVIG dose of 0.50 mg/g of body weight was given to mice at 1 h after ischemia, followed by a single i.v. injection of C1-INH at 75 U/kg 30 minutes later (n=19). The brain infarction volume was determined following a 72 hour reperfusion period and the percent inhibition of infarction volume was compared against the percent inhibition from C1-INH alone or IVIG alone.

DESCRIPTION OF ILLUSTRATIVE EMBODIMENTS

Reference will now be made in detail to certain exemplary embodiments according to the present disclosure, certain examples of which are illustrated in the accompanying drawings.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

The section headings are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

Disclosed are immunoglobulins and inhibitors of the complement protease C1. The combination of C1-Inhibitors such as C1-INH and immunoglobulins such as pooled intravenous immunoglobulin G (IVIG) can be used to treat, prevent, or reduce the inflammation damage and reperfusion injury associated with cerebral ischemia. In some embodiments, the use of a combination of C1-INH and immunoglobulins such as IVIG can be used to treat or prevent reperfusion injury and inflammation damage at later timepoints where either component alone provides less therapeutic or other beneficial effects. In some embodiments, the combination can be administered up to about 6 hours or longer after cerebral ischemia or at less than maximal doses of either component while providing beneficial effects. The combination can be used alone or additional therapeutic compounds can also be administered, such as compounds intended to remove or inhibit blood clot formation in the brain.

Immunoglobulin

As used herein, the terms "immunoglobulin" and "antibody" refer to any immunoglobulins (also known as antibodies) or fragments thereof that bind to active complement fragments in the brain and/or scavenge active complement fragments in the brain. The terms "antibody" and "immunoglobulin" in this context also comprise derivatives or fragments thereof which still retain some binding to complement fragments. Such fragments comprise, inter alia, Fab fragments, F(ab')$_2$, or Fc fragments. The antibodies may be derived from donor plasma or may be prepared using alternative methods (discussed infra), provided that they share with the plasma-derived antibodies a similar binding affinity for active complement fragments.

The term "complement fragments" refers to any circulating small molecule, protein, or enzyme associated with the signaling cascades involved in complement immunity. These cascades include the inflammatory, cytokine signaling, and other complement cascades known in the art.

The term "plasma-derived immunoglobulin" is intended to mean any polyclonal antibody fraction derived from mammalian, preferably human, plasma. In this regard, the term "antibody" may be interchangeably used with the term "immunoglobulin". In certain embodiments, the plasma of multiple (generally 1000 or more) healthy donors is pooled and optionally further processed. In some embodiments, the immunoglobulin fraction is enriched from the pooled plasma. Preferably, the immunoglobulin is purified from the pooled plasma. More preferably, the immunoglobulin is purified and concentrated. In various embodiments, purified and concentrated immunoglobulin G (IgG) is used. The plasma-derived immunoglobulins in this context also comprise derivatives or fragments thereof which still retain binding to complement fragments. Such fragments comprise, inter alia, Fab fragments, F(ab')$_2$, or Fc fragments. Also, the compositions comprising plasma-derived immunoglobulin can also include the addition of non-plasma-derived antibodies to the plasma-derived immunoglobulin.

The terms "intravenous immunoglobulin" refers to the intravenous delivery of a composition comprising immunoglobulin. Preferably, the intravenously delivered immunoglobulin is immunoglobulin G (IgG), more preferably plasma-derived IgG, even more preferably human-derived intravenous immunoglobulin G (IVIG). IVIG is a therapeutic preparation of pooled polyspecific immunoglobulin G obtained from the plasma of a large number of healthy individuals. The term "healthy individual" means an individual who meets the current (at the time of donation) standard eligibility criteria for donating blood, bearing in mind that such eligibility criteria are subject to continuous improvement and change.

In certain embodiments, IVIG may contain traces of immunoglobulins of different Ig classes such as IgA or IgM (preferably less than 2% of IgM or IgA, more preferably less than 1%). In various embodiments, the immunoglobulin will be >90% IgG, more preferably >95% IgG, even more preferably >98% IgG.

In other embodiments, the intravenously delivered immunoglobulin is immunoglobulin A (IgA) or immunoglobulin M (IgM), more preferably plasma-derived IgA or IgM, even more preferably human-derived intravenous IgA (IVIA) or IgM (IVIM). IVIA and IVIM are therapeutic preparations of pooled polyspecific immunoglobulin A or immunoglobulin M obtained from the plasma of a large number of healthy individuals, preferably at least 1000 individuals. In certain embodiments, IVIA or IVIM may contain traces of immunoglobulins of different Ig classes (preferably less than 2% of the other immunoglobulin classes, more preferably less than 1%). In various embodiments, the immunoglobulin will be >90% IgA or IgM, more preferably >95% IgA or IgM, even more preferably >98% IgA or IgM. In other embodiments, the intravenously delivered immunoglobulin is a combination of plasma derived IgG, IgM, and/or IgA. In certain embodiments, the combination intravenous immunoglobulin is at least 50% IgG, preferably at least 70% IgG, and more preferably at least 90% IgG.

IVIG denotes a product, as well as the preferred route of administration (intravenous administration). In a preferred embodiment, the IVIG is provided as a solution containing at least 5% (w/v) immunoglobulin in a total solution suitable for intravenous administration. In other embodiments, the IVIG is provided as a solution containing at least about 6% immunoglobulin, more preferably at least about 8%, 10%, 15%, 20%, or 25% immunoglobulin (or any percentage in between). The solution may contain additional ingredients such as stabilizers, for example amino acids such as proline or glycine, or sucrose, maltose, sorbitol, albumin, nicotinamide, PEG, or others.

In certain embodiments, the IVIG is PRIVIGEN® (CSL Behring) or SANDOGLOBULIN®/CARIMUNE® (CSL Behring). PRIVIGEN® is indicated as a replacement therapy for patients with primary immunodeficiency associated with defects in humoral immunity.

In other embodiments, the immunoglobulin is subcutaneous immunoglobulin G (SCIG). The term "subcutaneous immunoglobulin G," abbreviated SCIG, means a therapeutic preparation of pooled immunoglobulin G, similar to IVIG, but formulated for subcutaneous administration. SCIG also denotes a product as well as a preferred route of administration (subcutaneous administration). In certain embodiments, the SCIG is provided as a solution containing at least 10% (w/v) immunoglobulin, more preferably at least 15% immunoglobulin, most preferably about 20% immunoglobulin. The solution may contain additional ingredients such as stabilizers, for example amino acids such as proline or glycine, or sucrose, maltose, sorbitol, albumin nicotinamide, PEG, polysorbate 80, or others. In certain embodiments, the SCIG is VIVAGLOBIN® or HIZENTRA® (both CSL Behring).

In alternative embodiments, the present disclosure contemplates the use of non-plasma derived antibodies that share with the plasma-derived antibodies similar binding for active complement fragments (e.g., antibodies that act as scavengers of active complement fragments). The antibodies can be used either independently or as an additive to the plasma-derived immunoglobulin discussed above. These antibodies can be polyclonal or monoclonal. Antibodies that can be employed herein include those of Ig classes IgM, IgG, and IgA (preferably IgG). The term "antibody" also comprises derivatives or fragments thereof which still retain binding. Such fragments comprise, inter alia, Fab fragments, F(ab')$_2$, Fv fragments, scFv derivatives, or Fc fragments. The added antibodies also include embodiments such as recombinant, chimeric, humanized, carbohydrate-structure optimized, and fully human antibodies and fragments. Recombinant antibodies can also be further modified, e.g. by switching isotype, affinity maturation techniques, modifications to alter effector functions, modifications to alter glycosylation, etc.

C1 Inhibitor

The terms "C1 Inhibitor," "C1 esterase Inhibitor," and "C1-INH" refer to the proteins or fragments thereof that function as serine protease inhibitors to prevent spontaneous activation of circulating proteases associated with the complement system, preferably proteases C1r and C1s, as well as MASP-1 and MASP-2. In addition, C1-INH can serve as an anti-inflammatory molecule that reduces the selectin-mediated leukocyte adhesion to endothelial cells. C1-INH as used here can be a native serine protease inhibitor or active fragment thereof, or it can comprise a recombinant peptide, a synthetic peptide, a peptide mimetic, or a peptide fragment that provides similar functional properties—e.g., the inhibition of proteases C1r and C1s, and/or MASP-1 and MASP-2. For further disclosure regarding the structure and function of C1-Inhibitor, see U.S. Pat. Nos. 4,915,945; 5,939,389; 6,248,365; 7,053,176; and WO 2007/073186, which are hereby incorporated in their entirety.

Commercially available products comprising C1-inhibitor are, e.g. plasma-derived CINRYZE® (Viropharma), recombinant RUCONEST® or RHUCIN® (both Pharming), and plasma-derived BERINERT® (CSL Behring). BERINERT® is indicated for treatment of hereditary angioedema and congenital deficiencies.

Production of Immunoglobulin and C1-Inhibitor

In various embodiments, immunoglobulin and C1-Inhibitor can be produced according to methods known to one of skill in the art. For example, plasma-derived immunoglobulin as well as C1-INH can be prepared by collecting blood plasma from several donors. Donors of plasma should be healthy as defined in the art. Preferably, the plasma of several (1000 or more) healthy donors is pooled and optionally further processed. An exemplary process for preparing plasma-derived immunoglobulin (in this case, IVIG) can be found in US Application 2010/0330071 A1, the disclosure of which is hereby incorporated in its entirety. Examples of commercial IVIG products are PRIVIGEN® (CSL Behring) and SANDOGLOBULIN®/CARIMUNE®.

Techniques for the production of non-plasma-derived antibodies and fragments that bind active complement fragments are well known in the art and described in, e.g. Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. Also, transgenic animals may be used to express fully human antibodies or fragments thereof. For the preparation of monoclonal antibodies, any technique that provides antibodies produced by continuous cell line cultures can be used. Examples for such techniques include the hybridoma technique originally described by Köhler and Milstein, *Nature* 256: 495-497 (1975) further developed by the art to produce human antibodies. Also included are the trioma technique, the human B-cell hybridoma technique (Kozbor, *Immunology Today* 4: 72 (1983)), and the EBV-hybridoma technique to produce human monoclonal antibodies (Cole et al., *Monoclonal Antibodies and Cancer Therapy*, Alan R. Liss, Inc. (1985), 77-96). The non-plasma-derived antibodies may be expressed in cells, e.g. antibody nucleic acid constructs may be transfected and/or transduced via, amongst others, viruses or plasmid vectors. Other recombinant techniques for production in small or large scale may also be used.

Methods for preparing C1-INH are known in the art. For example, a process for producing C1-inhibitor for therapeutic purposes is disclosed in U.S. Pat. No. 4,915,945, the disclosure of which is hereby incorporated in its entirety. Alternatively, in some embodiments C1-INH can be collected and concentrated from natural tissue sources using techniques known in the art. Commercially available products comprising C1-inhibitor are, e.g. plasma-derived Cinryze® (Viropharma), recombinant Ruconest® or Rhucin® (both Pharming), and plasma-derived BERINERT® (CSL Behring) Recombinant C1-INH can be prepared by known methods.

Pharmaceutical Compositions

In certain embodiments, a pharmaceutical composition comprising C1-INH and a pharmaceutical composition comprising plasma-derived and/or non-plasma-derived immunoglobulin are prepared for use in the treatment of cerebral ischemia. Methods of formulating pharmaceutical compositions comprising C1-INH and pharmaceutical compositions comprising immunoglobulin are known in the art. For example, if a powder or lyophilized form of C1-INH or immunoglobulin (e.g., by freeze drying) is provided and an aqueous pharmaceutical is desired, the powder can be dissolved by mixing with aqueous components of the pharmaceutical formulation and stirred using suitable techniques such as vortexing or gentle agitation. Alternatively, if an aqueous pharmaceutical is desired and the C1-INH or immunoglobulin is already in aqueous form, the components can be directly combined prior to administration. In certain embodiments, C1-INH is provided in lyophilized form and combined with an aqueous immunoglobulin composition prior to administration to a patient. In other embodiments, immunoglobulin is provided in lyophilized form and combined with aqueous C1-INH composition prior to administration. In still other embodiments, both C1-INH are provided in lyophilized form and combined with aqueous pharmaceutical components (e.g., additional active components or inactive components such as fillers, stabilizers, solvents, or carriers) prior to administration. In yet other embodiments, both C1-INH and immunoglobulin are provided in aqueous solution and may be administered separately or may be combined prior to administration to a patient.

In certain embodiments, a pharmaceutical composition can comprise at least one additive such as a filler, bulking agent, buffer, stabilizer, or excipient. Standard pharmaceutical formulation techniques are well known to persons skilled in the art (see, e.g., 2005 *Physicians' Desk Reference©*, Thomson Healthcare: Montvale, N.J., 2004; *Remington: The Science and Practice of Pharmacy*, 20th ed., Gennado et al., Eds. Lippincott Williams & Wilkins: Philadelphia, Pa., 2000). Suitable pharmaceutical additives include, e.g., mannitol, starch, glucose, lactose, sucrose, gelatin, silica gel, sodium stearate, glycerol monostearate, talc, sodium chloride, glycerol, propylene, glycol, water, ethanol, and the like. In certain embodiments, the pharmaceutical compositions may also contain pH buffering reagents and wetting or emulsifying agents. In further embodiments, the compositions may contain preservatives or stabilizers.

The formulation of pharmaceutical compositions may vary depending on the intended route of administrations and other parameters (see, e.g., Rowe et al., *Handbook of Pharmaceutical Excipients*, 4th ed., APhA Publications, 2003.) In some embodiments, the pharmaceutical composition may be a lyophilized cake or powder. The lyophilized composition may be reconstituted for administration by intravenous injection, for example with Sterile Water for Injection, USP. In other embodiments, the composition may be a sterile, non-pyrogenic solution. In still further embodiments, the composition is delivered in powder form in a pill or tablet.

The described pharmaceutical compositions may comprise C1-INH and/or immunoglobulin as the sole active compounds or may be delivered in combination with at least one other compound, composition, or biological material. Examples of such compounds include vitamins, antibiotics, or compounds intended to remove or inhibit blood clot formation in the brain (e.g., aspirin, clopidogrel, or dipyridamole).

Also disclosed are kits for the treatment of cerebral ischemia. In certain embodiments, the kits comprise (a) an immunoglobulin such as IVIG; (b) C1-INH, (c) instructions for use in the treatment of cerebral ischemia and optionally (d) at least one further therapeutically active compound or drug.

The components of the kit may be contained in one or different containers such as one or more vials. The antibodies may be in liquid or solid form (e.g. after lyophilization) to enhance shelf-life. If in liquid form, the immunoglobulin may comprise additives such as stabilizers and/or preservatives such as proline, glycine, or sucrose or other additives that enhance shelf-life. Likewise, the C1-INH may be in liquid or solid form (e.g. after lyophilization). If in liquid form, the C1-INH may comprise additives such as stabilizers and/or preservatives such as proline, glycine, or sucrose or other additives that enhance shelf-life.

In certain embodiments, the kit may contain additional compounds such as therapeutically active compounds or drugs that are to be administered before, at the same time or after administration of the immunoglobulin and the C1-INH. Examples of such compounds include vitamins, antibiotics, anti-viral agents, etc. In other embodiments, compounds intended to remove or inhibit blood clot formation in the brain (e.g., aspirin, clopidogrel, or dipyridamole) can be included with the kit.

In various embodiments, instructions for use of the kits will include directions to use the kit components in the treatment of cerebral ischemia. The instructions may further contain information regarding how to prepare (e.g. dilute or reconstitute, in the case of freeze-dried protein) the immunoglobulin and the C1-Inhibitor. The instructions may further include guidance regarding the dosage and frequency of administration.

Methods of Treatment

In certain embodiments, methods of treating, preventing, or reducing the effects of cerebral ischemia are provided. The term "cerebral ischemia," as used herein, refers to any condition in which there is insufficient blood flow to at least a portion of the brain due to occlusion of one or more brain arteries. The definition encompasses both focal and global ischemia. The term encompasses all medical causes of insufficient blood flow, for example, cerebral hypoxia, traumatic brain injury, and stroke (including thrombosis, cerebrovascular embolism, ischemic stroke, perinatal stroke, and cerebral infarction).

For example, treatment of cerebral ischemia can comprise administering to a patient C1-INH and an immunoglobulin that scavenges active complement fragments in the brain. Preferably, the immunoglobulin is IVIG. In some embodiments, the combination is administered to prevent, treat, or reduce the effects of inflammation damage or reperfusion injury following cerebral ischemia. The immunoglobulin and C1-Inhibitor can be administered together or separately. The compounds can be administered by any suitable delivery route and may include, without limitation, parenteral, subdural, intramuscular, intrathecal, or intraperitoneal injection. In certain embodiments where the immunoglobulin is IVIG, the compound is delivered intravenously. In other embodiments where the immunoglobulin compound is SCIG, the compound is delivered subcutaneously.

The immunoglobulin and the C1-INH may be administered together or separately. In certain embodiments, the C1-INH and immunoglobulin are administered together in a single intravenous administration. In other embodiments, the immunoglobulin is administered first, followed by administration of the C1-INH. In certain embodiments, the C1-INH is administered approximately 5, 10, 20, 30, 40, 50, 60, 90, or 120 minutes after administration of immunoglobulin (or at any time in between). In other embodiments, the C1-INH is administered first, followed by administration of the immunoglobulin. In certain embodiments, the immunoglobulin is administered approximately 5, 10, 20, 30, 40, 50, 60, 90, or 120 minutes after administration of C1-INH (or at any time in between).

Treatment with C1-INH and an immunoglobulin such as IVIG can occur immediately or up to about six hours following cerebral ischemia. In certain embodiments, treatment occurs about 10, 20, 30, 40, or 50 minutes, or 1, 2, 3, 4, 5, or 6 hours following cerebral ischemia (or at any time in between). Treatment even after 6 hours following stroke may have benefits (e.g., at about 7, 8, 9, 10, 15, 18, or 24 hours following cerebral ischemia, or at any time in between). In some embodiments, the use of a combination of C1-INH and immunoglobulins such as IVIG can be used to treat or prevent reperfusion injury and inflammation damage at later timepoints where either component alone provides for less therapeutic or other beneficial effects. In some embodiments, the combination can be administered at less than maximal doses of either component while providing for beneficial effects. In some embodiments, administration of combination therapy after about 3 hours following cerebral ischemia (e.g., up to about 6 hours) can yield beneficial effects that exceed those observed when either immunoglobulin or CI-INH is administered on its own at these later timepoints.

Administration to a patient may occur in a single dose or in repeat administrations, and in any of a variety of physiologically acceptable forms, and/or with an acceptable pharmaceutical carrier and/or additive as part of a pharmaceutical composition.

The composition comprising C1-INH and the composition comprising an immunoglobulin such as IVIG may be administered to a patient in therapeutically effective amounts. Generally, a therapeutically effective amount may vary with the subject's age, general condition, and gender, as well as the severity of the medical condition in the subject. The dosage may be determined by a physician and adjusted, as necessary, to suit the observed effects of the treatment. In certain embodiments, the dose of C1-INH may range from approximately 0.01 U/kg to 2000 U/kg of bodyweight. In various embodiments, the dose of C1-INH is 0.01, 0.05, 0.10, 0.50, 1.0, 5.0, 10, 15, 20, 25, 30, 50, 75, 100, 125, 150, 175, 200, 225, 250, 275, 300, 325, 350, 375, 400, 450, 500, 1000, 1500, or 2000 U/kg of bodyweight (or any value in between). Exemplary therapeutic ranges for C1-INH administration are also disclosed in U.S. Pat. No. 5,939,389, the disclosure of which is incorporated in its entirety. In some embodiments, the immunoglobulin is IVIG and the dose is 0.01, 0.05, 0.10, 0.20, 0.25, 0.5, 0.75, 1.0, 1.25, 1.5, 1.75, 2.0, 2.25, 2.5, 2.75, or 3.0 g/kg of bodyweight (or any value in between). Exemplary therapeutic ranges for IVIG administration are also disclosed in Arumugam et al., *PNAS* 104(35): 14104-14109 (2007), the disclosure of which is hereby incorporated in its entirety.

The administered pharmaceutical compositions may comprise C1-INH and/or immunoglobulin as the sole active compounds or may be delivered in combination with at least one other compound, composition, or biological material. Examples of such compounds include vitamins, antibiotics, or compounds intended to remove or inhibit blood clot formation in the brain (e.g., aspirin, clopidogrel, or dipyridamole).

In certain embodiments, treatment of cerebral ischemia using a combination of C1-INH and an immunoglobulin can potentiate the therapeutic effect of either C1-INH or immunoglobulin therapy in isolation. In some embodiments, combination therapy results in an additive effect on the reduction in infarct volume or neurological deficit following cerebral ischemia. In further embodiments, the combination acts synergistically to enhance the effect seen with either C1-INH or immunoglobulin therapy in isolation. In certain embodiments, combination therapy increases the reduction in brain infarction volume observed with C1-INH therapy alone by 5%, 10%, 15%, 20%, 25%, 30%, 35%, 40%, 45%, 50%, 55%, 60%, 65%, 70%, 75%, 80%, 85%, or 90% (or any percent in between). In some embodiments, combination therapy increases the reduction in brain infarction volume observed with immunoglobulin therapy alone by 5%, 10%, 15%, 20%, 25%, 30%, 35%, 40%, 45%, 50%, 55%, 60%, 65%, 70%, 75%, 80%, 85% (or any percent in between), or produces a reduction of infarct volume at least about equivalent to the reduction observed when an optimal concentration of immunoglobulin is administered on its own following cerebral ischemia.

In certain embodiments, administration of C1-INH and IVIG in combination reduces the infarct volume to about one-half or one-third of that observed when C1-INH is administered on its own following cerebral ischemia. In some embodiments, administration of a combination of C1-INH and IVIG reduces the infarct volume to about one-half of that observed when IVIG is administered on its own following cerebral ischemia, or reduces the infarct volume to at least about equivalent to that observed when an optimal concentration of IVIG is administered on its own following cerebral ischemia.

In certain embodiments of the combination therapy, C1-INH and IVIG are administered at reduced dosages, as compared to the optimal concentration when administered individually. In these embodiments, the combination therapy enables the use of reduced concentrations while maintaining therapeutic or other beneficial effects, thereby reducing cost and the risk of adverse reaction to the therapeutic agents. In addition, in certain embodiments, the administration of combination therapy at reduced dosages can help reduce or avoid the risk of hemorrhage associated with high doses of C1-INH or IVIG. Bundesarztekammer, *Dtsch Arztebl* 97: B-864 (2000), Stieh et al., *Biomed Prog.* 9:13-16 (1996), Horstick et al., *Circulation* 104: 3125-3131 (2001). In certain embodiments, the use of reduced dosages could also lead to increased patient tolerance. In some embodiments, an effective treatment regimen for acute ischemic stroke can consist of IVIG treatment initially, followed by the administration of one or more early-acting therapeutics (e.g., inhibitors of sodium or calcium channels), and finally administration of the combination of IVIG/C1-INH.

In treating human stroke victims the patients should be treated according to the established standard of care. In particular, where possible the patient should be examined by MRI or other methods to determine whether the brain injury is ischemic or hemorrhagic, since the administration of IVIG or C1-INH may be contraindicated where the brain injury is hemorrhagic.

EXAMPLES

The following examples serve to illustrate, and do not limit, the present disclosure.

Example 1

C1-INH Dose-response

Brain ischemia/reperfusion (I/R) injury was induced by 1 hour occlusion of the middle cerebral artery (MCAO) of mice followed by a 72-hour reperfusion. Arumugam et al., *PNAS* 104: 14104-14109 (2007); Wang et al., *Eur. J. Neu-* rosci. 28(1): 51-61 (2008). In non-treated (I/R only) mice this procedure resulted in an average brain infarction of 36% of the affected hemisphere.

Figure 1:
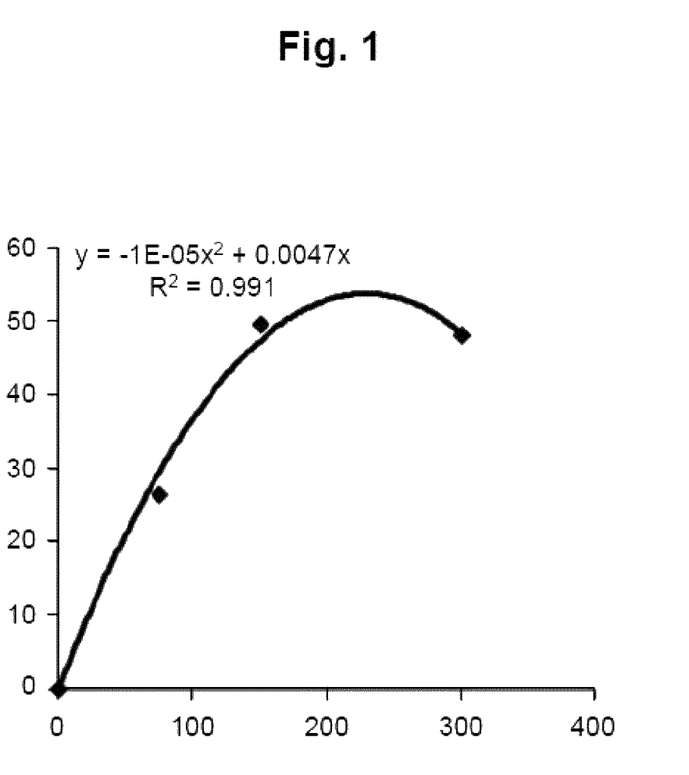

To evaluate the effect of C1-INH concentration, groups of mice (n=12-21) were treated at 1 hour after the end of the ischemic period with decreasing doses of C1-INH (BERINERT®, CSL Behring) at 300 U/Kg (7.6 U per animal), 150 U/Kg (3.8 U per animal) and 75 U/Kg (1.9 U per animal). The maximum effect on the reduction of brain infarction size (50%) peaked at 150 U/Kg, with the $IC_{50}$ effect (25% reduction) achieved with 75 U/Kg or 1.9 U/animal. See FIG. 1.

A single dose of C1-Inhibitor at 300 U/kg, administered 30 min before ischemia and during reperfusion at 1 h, 3 h, and 6 h post-ischemia, reduced brain infarction size relative to vehicle-treated mice by 69%, 48%, 50% and 67%, respectively. C1-INH treatment also significantly reduced functional impairment, as shown by reduced neurological deficit scores (at 48 h and 72 h after MCAO) in comparison to mice that received vehicle alone. Reduction of the C1-INH dose to 150 U/kg and 75 U/kg did not result in corresponding incremental worsening of the experimental stroke endpoints, as seen in the IVIG dose-response experiment. Instead, there was no significant difference in the degree of inhibition of brain infarction, neurological deficit at 72 hours post-ischemia, and mortality among the three doses of C1-INH.

Example 2

IVIG Dose Response

Figure 2:
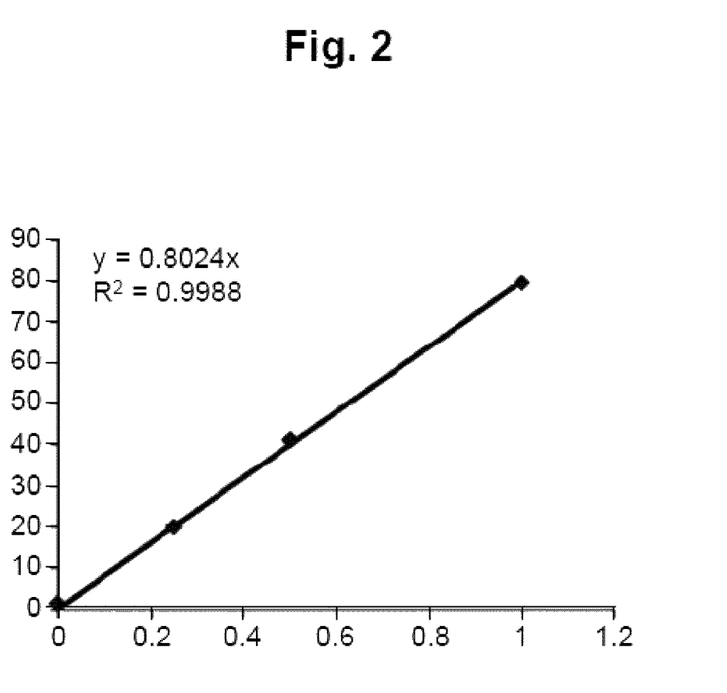

Groups of animals (n=12-22) were treated 1 hour after ischemia with decreasing doses of IVIG (PRIVIGEN®, CSL Behring), starting with 1 g/kg of body weight and continuing with steadily decreasing half doses—0.5 g/Kg and 0.25 g/Kg (or as measured in mg/g considering the average body weight of an adult mouse to be 25-30 g). There was a linear correlation between decreasing IVIG dose and reduction of brain infarction size. The $IC_{50}$ value was around 0.5 g/Kg (mg/g). See FIG. 2.

IVIG treatment (1 g/kg) 30 min before and 1 h after MCAO, as well as 3 h and 6 h post ischemia (2 g/kg) reduced the infarction size by 56%, 80% 58% and 59%, respectively. Treatment with control reagents, 250 mM L-proline (which serves as a vehicle or stabilizer for immunoglobulin molecules in PRIVIGEN®) or human albumin (for IV use) at 1 g/kg in vehicle solution, had no significant effect on the size of infarction when compared to non-treated mice.

To determine if the marked reduction of ischemic brain injury observed in IVIG-treated mice resulted in reduced functional impairment, neurological deficits were evaluated daily at 24, 48, and 72 hours after MCAO in mice that were eventually sacrificed to obtain brain infarction measurements. Murakami et al., J. Neurosci. 18: 205-213 (1998). IVIG treatments significantly reduced the neurological deficits at 48 and 72 hours after ischemia. IVIG also exerted a dose-dependent effect on the consequences of ischemic brain injury. With half-decreasing doses of PRIVIGEN® (1.0 g/kg, 0.5 g/kg and 0.25 g/kg), a stepwise increase in brain infarction size, neurological deficit at 72 h, and mortality were observed.

Example 3

Therapeutic Window of BERINERT®

Mice subjected to experimental stroke were treated with BERINERT® at 150 U/Kg (3.8 U per animal) 3 hours after the completion of ischemia. Brain infarction size was measured and infarction size reduction was determined. Reduction in infarction size resulting from treatment 3 hours after completion of ischemia was not statistically different from the effect of the same dose when administered one hour after ischemia (approximately 50% reduction of brain infarction). This finding is in contrast to earlier published results by De Simoni et al., The Powerful Neuroprotective Action of C1-Inhibitor on Brain Ischemia-Reperfusion Injury Does Not Require C1 q, Am. J. Pathol. 164: 1857-63 (2004), indicating that plasma-derived C1-INH (Baxter-Immuno, Pisa, Italy) had a therapeutic window of only one hour after brain ischemia.

Example 4

Combination C1-INH and IVIG Treatment

Figure 3:
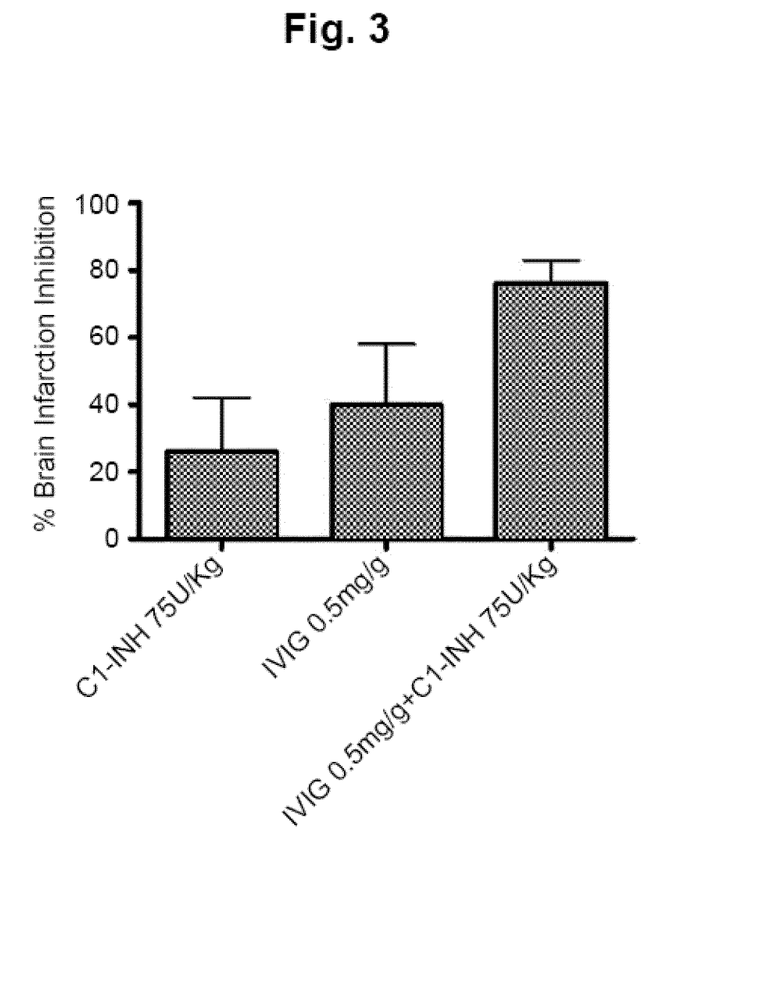

To determine the neuroprotective potential of IVIG and C1-INH as a combined treatment, a single dose of 0.50 mg/g IVIG was given to mice at 1 h after ischemia, followed by a single i.v. injection of C1-INH at 75 U/kg 30 minutes later (n=19). The brain infarction volume was determined following a 72 hour reperfusion period. The combined treatment potentiated the effect of 75 U/Kg dose of C1-INH almost 3 times (from 26% to 76%) and roughly doubled (from 40% to 76%) the effect of 0.5 mg/g of IVIG on the reduction of brain infarction volume. The combined treatment was more neuroprotective when compared to the optimal C1-INH dose (300 U/kg). The combined treatment reduced both mortality rate and the infarction size by about 50% relative to animals infused with 300 U/kg of C1-INH. The combined treatment was as effective as the optimal dose of IVIG (1 g/kg)—mortality rates and infarction sizes did not significantly vary between the two groups of animals. See FIG. 3. The neurological deficit was significantly reduced at all time points (24, 48, and 72 hours post ischemia) in mice receiving both IVIG and C1-INH, in comparison to the I/R only group and 17%-24% lower than in mice treated with the suboptimal doses of IVIG (0.50 mg/g) or C1-INH (75 U/kg) alone.

Figure 4A:
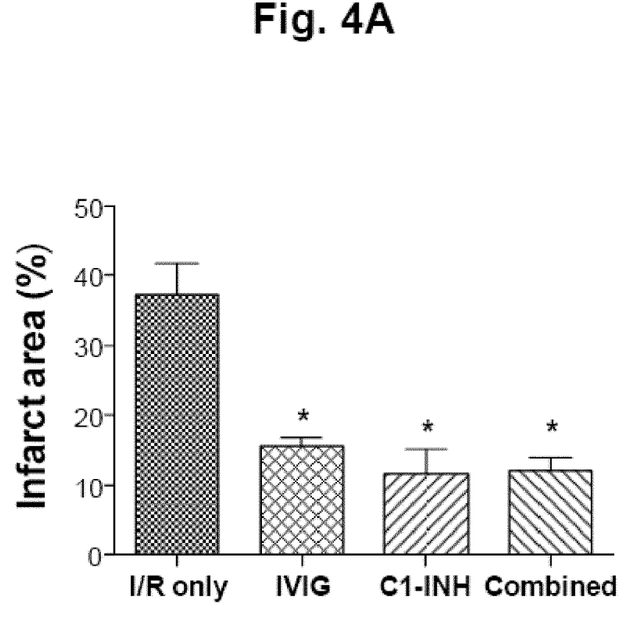
FIGS. 4a-b. Mice were treated with IVIG at 1 g/kg (n=11), C1-INH at 300 U/kg (n=9) or the combination (n=10) six hours after the beginning of ischemia and the infarction area (FIG. 4a) and neurological deficit score (FIG. 4b) were determined at 72 hours post ischemia (*P<0.001).
Figure 4B:
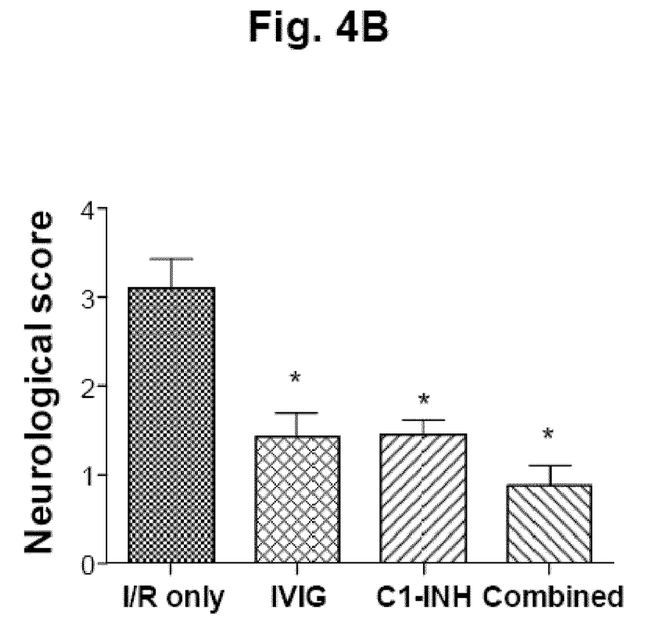

The combined administration was equally effective as IVIG or C1-INH alone in terms of reducing the size of brain infarction (by 67% in comparison to non-treated animals), even when applied 6 hours after ischemia. FIG. 4a. Following combined treatment at 6 h post-ischemia, the neurological disabilities score improved by 71%. This effect was significantly more pronounced compared to mice treated with optimal individual doses of IVIG or C1-INH. FIG. 4b.

Example 5

IVIG and C1-INH Protect Older Mice and Female Mice from Injury

Human stroke affects both sexes equally, and its incidence rises with age. For that reason we tested the effectiveness of IVIG, C1-INH and the combined treatment in female mice. We also tested the effects in 13-14 month-old male mice (older than previously tested) 6 hours post ischemia. Both older male mice and female mice exhibited significantly reduced infarction size and the degree of neurological disabilities at 72 hours after ischemia compared to non-treated animals, when infused with IVIG alone at 1 g/kg, C1-INH alone at 300 U/kg, as well as with half-maximal inhibitory (IC50) concentrations of both administered in succession. In older mice, combined therapy was approximately 50% and 70% more effective in terms of reducing the infarction size and neurological deficit score.

Example 6

IVIG and C1-INH Reduce In-Situ Accumulation of C3b

The effect of combined IVIG/C1-INH treatment on the levels of C3b, the active fragment of the third complement component, in brain samples from mice subjected to I/R injury was evaluated. Basal levels of C3b observed in brains of normal and sham-operated animals were similar to the C3b level in the contralateral (non-injured) hemisphere of I/R mice. Following I/R injury, C3b at the site of injury (in the ipsilateral hemisphere) was increased 5-fold in the cortex and 15-fold in the striatum. Both IVIG (at 1.0 g/kg) and C1-INH (at 300 U/kg), administered 1 h after the onset of reperfusion, reduced C3b expression by approximately 3-fold in both the cortex and striatum of the affected hemisphere. This data suggests that the complement system is activated in response to brain ischemia, leading to in-situ deposition of active fragments. Both complement scavenging and inhibition appear to be effective in reducing neuronal damage triggered by C3b deposition. More pronounced deposition of C3b in the striatal portion of the infarction correlates with previous findings of more extensive anatomical damage in that area, providing further evidence of a cause-and-effect relationship between I/R brain injury and complement activation.

Example 6

Complement Activation Upregulates TLR2 in Ischemic Stroke

The complement system and Toll-like receptors (TLRs) represent the front line of the host's innate immune defense system, and react to invading pathogens and altered self-antigens via pattern recognition. The possible co-activation of complement and TLR pathways during ischemic stroke was therefore evaluated. Attenuation of both pathways by IVIG and C1-INH was evaluated by performing double-label immunohistochemistry using antibodies against C3b and TLR2. In tissue sections taken from the penumbra region of the brain 24 h after I/R injury, over 90% of the brain cells showed levels of intrinsic C3 and TLR2 expression that were 11 (C3) and 28 (TLR2) times higher than in the same sections taken from sham-operated animals, as determined by quantifying pixel intensity of the antibody signals. In mice treated with IVIG (1 g/kg) and C1-INH (300 U/kg) 1 hour post ischemia, both C3 and TLR2 signals were significantly suppressed. Double-label immunofluorescence staining for C3 and TLR2 revealed that, in almost all brain cells, these two molecules co-localize. In sections from mice treated with both IVIG and C1-INH, the co-localized signal was suppressed as effectively as the individual signals.

Example 7

Comparison of IVIG Therapy, C1-INH Therapy, and Combination Therapy

Both IVIG (PRIVIGEN®, CSL Behring) and C1-INH (BERINERT®, CSL Behring) significantly reduced brain infarction size, neurological deficit score, and deposition of C3b fragments at the site of injury in a dose responsive manner when given 30 minutes before or 1 hour after ischemia. The optimal dose of IVIG exerted more neuroprotection than the optimal dose of C1-INH (85% vs. 48% reduction of brain infarction volume and 35% vs. 22% inhibition of neurological deficit, respectively). Treatment with human serum albumin and vehicles (stabilizing solutions) for IVIG and C1-INH did not improve the magnitude of brain injury observed in non-treated controls. This data suggests that complement attenuation could be considered as a novel interventional therapy for stroke.

C1-INH inhibits complement activation, but does not neutralize already generated complement activation fragments, while IVIG does not inhibit new complement activation but does scavenge activated complement fragments. In a complement-mediated disease, such as stroke, new bouts of complement activation occur sporadically, generating new pathogenic complement products. A combination of an inhibitor and a scavenger provides an improved therapeutic strategy for removing existing active fragments and preventing further complement activation. The combination of suboptimal doses of both IVIG and C1-INH not only exceeded the effects of the individual concentrations, but also exceeded the optimal C1-INH concentration and equaled the therapeutic potential of IVIG at 1 g/kg, except in older mice where combined treatment exhibited superior brain protection compared to IVIG alone.

Combination therapy could provide benefit for the treatment of stroke in humans, since both IVIG and C1-INH are already used in the treatment of other human disorders and have been shown to be safe.

Example 8

Materials and Methods

Focal Cerebral Ischemia/Reperfusion Model. All experimental protocols and procedures were approved by the Animal Care and Use Committee of the National Aging Institute and were conducted in compliance with the NIH Guide for the Care and Use of Laboratory Animals. Three-month-old male C57BL/6 mice (25-30 g) were anesthetized with isoflurane (induction 5.0%, maintenance 1.5-2.0%). The animals were then subjected to transient middle cerebral artery occlusion (TMCAO), using the intraluminal filament method. Briefly, the left common carotid artery, external carotid artery (ECA) and internal carotid artery (ICA) were exposed via a midline neck incision. Then, a silicon-coated monofilament (diameter with coating 0.23+/−0.02 mm) was introduced into the ECA lumen through an incision and advanced from the ECA to the ICA lumen until light resistance was felt. The monofilament was removed after a period of 1 h to initiate reperfusion for up to 72 h. Sham-operated mice were treated identically with the exception of the insertion of the filament to produce an occlusion.

Treatment regimen. The IVIG preparation (PRIVIGEN®, CSL Behring AG, Bern, Switzerland) used in these examples was a 10% protein solution containing >98% IgG, and <0.025 mg/ml IgA. IgG molecules in PRIVIGEN® are stabilized with 250 mmol/L L-proline (vehicle). Lyophilized, plasma-derived human C1s esterase inhibitor, C1-INH (BERINERT®, CSL Behring GmbH, Marburg, Germany), was reconstituted with 10 ml of sterile water to achieve a final C1-INH dose of 500 U in vehicle solution containing 10 mg/ml of glycine, 8.5 mg/ml of NaCl and 3 mg/ml of sodium citrate. Reconstituted C1-INH was kept at +4° C. and used within 14 days. Both IVIG and C1-INH were administered by slow infusion into the femoral vein either 30 min before (pre treatment) or at designated time points (1 h and 3 h post treatment) after MCAO. Vehicle solutions for both therapeutics (as described in the above examples) were infused into control animals at a volume equal to that in which optimal doses of IVIG and C1-INH were delivered.

Neurological deficit evaluation. At designated post-stroke time points, the functional consequences of focal cerebral I/R injury were evaluated using a six-point neurological deficit score (0, no deficit; 1, failure to extend right paw; 2, circling to the right; 3, falling to the right; 4, unable to walk spontaneously and 5, dead). Each mouse was assessed in a blinded fashion by at least two investigators.

Quantification of cerebral infarction. Mice were anesthetized, decapitated, and their brains removed. Two-millimeter coronal slices were prepared using a rodent brain matrix (Kent Scientific, Torrington, Conn.) and stained for 20 min at 37° C. with 2% 2,3,5-triphenyltetrazolium chloride monohydrate (TTC, Sigma, St Louis, Mo.) in phosphate buffer. The sections were scanned and the infarction size was evaluated using NIH image analysis software (ImageJ; National Institutes of Health, Bethesda, Md.).

Gel Electrophoresis and Western Blotting. Brain cortical and striatal samples from IVIG- and C1-INH-treated mice, and appropriate vehicle control mice, were placed in lysis buffer containing 300 mM NaCl, 1.5 mM $MgCl_2$, 25 mM HEPES, 20 mM β-glycerophosphate, 0.2 mM EDTA, 0.5 mM dithiothreitol (DTT) and 0.1% Triton-X with protease inhibitors. Tissues were lysed by 30-second sonication at 4° C. using an ultrasonic processor (VC 130 PB, Sonic & Materials Inc., Newtown, Conn.) and the cellular extracts were centrifuged for 5 minutes at 18,000×g. Protein content was then determined by a bicinchoninic acid (BCA) assay kit from Bio-Rad (Hercules, Calif.). Supernatant samples were separated on 10% SDS gels and the resolved proteins electrophoretically transferred to a 0.45 μm polyvinylidene fluoride (PVDF) membrane (Millipore Corporation, Bedford, Mass.). The blots were incubated with a primary anti-C3b antibody (Cell Sciences, Canton, Mass.) and an anti-β actin monoclonal antibody (Sigma Chemical Co., St. Louis, Mo.) overnight at 4° C. Following incubation with horseradish peroxidase-conjugated secondary IgG for 1 hour, reaction products were visualized using an enhanced chemiluminescence assay (Amersham Corporation, Piscataway, N.J.). Relative changes in protein expression were estimated from the mean pixel density of each protein band using the Scion Image program (Orem, Utah).

Immunohistochemical evaluation. Mice designated for immunohistochemical studies were deeply anaesthetized after 24 hours of reperfusion, and transcardially perfused with PBS until the outflow ran clear. Fixation was achieved with 4% paraformaldehyde in PBS. Brains were dissected out and placed in the same fixative overnight at 4° C. The frontal brain was processed for paraffin sectioning. Serial coronal sections were cut (5 μm thick) and mounted on glass slides. Sections were deparaffinized, rehydrated, and subjected to antigen retrieval using high-pH TRIS-EDTA buffer. All cell counts were carried out in defined areas maintained across all sections. Following blockade of nonspecific antibody binding, sections were incubated overnight with primary rabbit polyclonal anti-C3 antibody (Santa Cruz Biotechnology, Santa Cruz, Calif.) and rat monoclonal anti-TLR2 (Biolegend, CA) at 4° C. After being incubated with appropriate Alexa Fluor 568 (red fluorescence) and Alexa Fluor 488 (green fluorescence) conjugated secondary antibodies (Invitrogen, Carlsbad, Calif.) for 45 min and counterstained with Hoechst 33258, images were acquired with an Olympus fluorescence microscope. Images were processed with Photoshop 7.0 (Adobe Systems, San Jose, Calif.) with the input levels adjusted to span the range of acquired signal intensities. Pixel intensity was quantified using IP Labs Software (BD Biosciences, San Diego, Calif.).

Statistical Analysis. Statistical comparisons were made using Student's t test, Fisher's exact test, ANOVA, and Newman-Keuls post hoc tests for pairwise comparisons.

The preceding examples are intended to illustrate, and do not limit the present disclosure. Other embodiments of the disclosed devices and methods will be apparent to those skilled in the art from consideration of the specification and practice of the devices and methods disclosed herein.

The invention claimed is:

1. A method of treating or reducing the effects of inflammation damage or reperfusion injury following cerebral ischemia, comprising administering to a patient in need thereof a composition comprising human plasma derived immunoglobulin G as intravenous immunoglobulin G (IVIG) or subcutaneous immunoglobulin G (SCIG), and a composition comprising C1-Inhibitor (C1-INH), wherein the IVIG is administered at a dose from 0.05 g/kg to 0.5 g/kg of bodyweight, and the C1-INH is administered at a dose of approximately 75 U/kg of bodyweight.

2. The method of claim 1, wherein the immunoglobulin G and C1-INH are administered at sufficient dosages such that the combination of the immunoglobulin G and C1-INH produces at least about a 50% reduction in infarct volume, as compared to when C1-INH is administered on its own following cerebral ischemia.

3. The method of claim 1, wherein the immunoglobulin G and C1-INH are administered at sufficient dosages such that the combination of the immunoglobulin G and C1-INH produces a reduction of infarct volume at least about equivalent to the reduction observed when the same dose of the immunoglobulin G is administered on its own following cerebral ischemia.

4. The method of claim 1, wherein the immunoglobulin G and C1-INH are administered at sufficient dosages such that the combination produces at least a 40% reduction in infarct volume, as compared to infarct volume in the absence of treatment.

5. The method of claim 1, wherein the immunoglobulin G and the C1-INH are administered at the same time.

6. The method of claim 1, wherein the immunoglobulin G and the C1-INH are administered sequentially, with either the immunoglobulin G administered first or the C1-INH administered first.

7. The method of claim 6, wherein the C1-INH is administered at least 10 minutes after the immunoglobulin G.

8. The method of claim 6, wherein the immunoglobulin G is administered at least 10 minutes after the C1-INH.

9. The method of claim 1, wherein the combination of immunoglobulin G and C1-INH is administered up to about six hours following cerebral ischemia.

10. The method of claim 1, wherein the immunoglobulin G and C1-INH are administered intravenously.

11. The method of claim 1, wherein the immunoglobulin G and C1-INH are provided in aqueous or lyophilized form.

12. The method of claim 11, wherein the immunoglobulin G and C1-INH in lyophilized form are reconstituted prior to administration by dissolving them in a pharmaceutically-acceptable carrier.

13. The method of claim 12, wherein the pharmaceutically-acceptable carrier is sterile water for injection.

14. The method of claim 1, wherein the immunoglobulin G and C1-INH are administered at dosages lower than the dosages for independent administration.

15. The method of claim 14, wherein the combined administration of immunoglobulin G and C1-INH produces a reduction in infarct volume or a reduction in neurological deficit at least about equivalent to the reduction observed when either the immunoglobulin G or C1-INH is administered at the same dose on its own.

16. The method of claim 14, wherein the immunoglobulin G and C1-INH are administered at dosages that reduce the risk of cerebral hemorrhage.

17. The method of claim 1, wherein the combination of immunoglobulin G and C1-INH is administered up to about 18 hours following cerebral ischemia.

* * * * *